United States Patent
Popescu et al.

(10) Patent No.: US 7,522,698 B2
(45) Date of Patent: Apr. 21, 2009

(54) FOCUS/DETECTOR SYSTEM OF AN X-RAY APPARATUS FOR GENERATING PHASE CONTRAST RECORDINGS

(75) Inventors: Stefan Popescu, Erlangen (DE); Björn Heismann, Erlangen (DE); Eckhard Hempel, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/700,042

(22) Filed: Jan. 31, 2007

(65) Prior Publication Data

US 2007/0183562 A1    Aug. 9, 2007

(30) Foreign Application Priority Data

Feb. 1, 2006    (DE) .................. 10 2006 004 976
Apr. 3, 2006    (DE) .................. 10 2006 015 358

(51) Int. Cl.
*H05G 1/60* (2006.01)
*H05G 1/64* (2006.01)

(52) U.S. Cl. ........................ 378/19; 378/98.8
(58) Field of Classification Search ............ 378/2, 378/4, 19, 62, 70, 71, 84–87, 145; 250/370.09
See application file for complete search history.

(56) References Cited

U.S. PATENT DOCUMENTS

| | | | |
|---|---|---|---|
| 5,812,629 A | 9/1998 | Clauser | |
| 2005/0286680 A1 | 12/2005 | Momose | |
| 2007/0183560 A1 | 8/2007 | Popescu et al. | |
| 2007/0183580 A1* | 8/2007 | Popescu et al. | 378/145 |
| 2007/0183581 A1* | 8/2007 | Heismann et al. | 378/145 |
| 2007/0183583 A1* | 8/2007 | Baumann et al. | 378/145 |
| 2007/0183584 A1 | 8/2007 | Baumann et al. | |

FOREIGN PATENT DOCUMENTS

| | | |
|---|---|---|
| DE | 10 2006 015 355.3 | 8/2007 |
| DE | 10 2006 015 356.1 | 8/2007 |
| DE | 10 2006 015 358.8 | 8/2007 |
| DE | 10 2006 017 290.6 | 8/2007 |

(Continued)

OTHER PUBLICATIONS

Weitkamp, T., (u.a.): X-ray phase imaging with a grating interferometer. Optics Express, 2005, vol. 13, No. 16, S. 6296-6304.

(Continued)

*Primary Examiner*—Irakli Kiknadze
(74) *Attorney, Agent, or Firm*—Harness, Dickey & Pierce, P.L.C.

(57) ABSTRACT

A focus/detector system of an X-ray apparatus is disclosed, for generating projective or tomographic phase contrast recordings. The system, in at least one embodiment, includes at least of a beam source, having a focus and a focus-side source grating, arranged in the beam path and to generate a field of ray-wise coherent X-rays, and a detector arrangement having a multiplicity of grating/detector modules arranged next to one another. The detector arrangement, in at least one embodiment, which respectively include, arranged successively in the beam direction, at least one phase grating for generating a first interference pattern, an analysis grating for generating a further interference pattern, and detector elements arranged flat. The individual grating lines of all gratings are aligned mutually parallel.

24 Claims, 3 Drawing Sheets

FOREIGN PATENT DOCUMENTS

| DE | 10 2006 017 291.4 | 8/2007 |
|---|---|---|
| EP | 1 447 046 A1 | 8/2004 |
| EP | 1 731 099 A1 | 12/2006 |
| WO | WO 2004/071298 A1 | 8/2004 |

OTHER PUBLICATIONS

Pfeifer, F., Weitkamp T. et al: Phase retrieval and differential phase-contrast imaging with low-brillance X-ray sources. Nature Physics, 2006, vol. 2, S. 258-261.

Weitkamp et al., "X-ray phase imaging with a grating interferometer", Optics Express 2005, vol. 12, No. 16, pp. 6296-6304.

D. Vaughan (ed.), "X-Ray Data Booklet", Lawrence Berkeley Laboratory, Berkley, 1986, pp. 2-28, 2-29.

U. Bonse and M. Hart, "An X-ray Interferometer", Appl. Phys. Lett., 1965, vol. 8, pp. 155-156.

Ingal and Beliaevskaya, "X-ray plane-wave topography observation of the phase contrast from a non-crystalline object", J. Phys. D: Appl. Phys. 28, 1995, pp. 2314-2317.

R. Fitzgerald, "Phase-Sensitive X-Ray Interferometer", Physics Today, 53, 2000, pp. 23-26.

Chapman et al., "Diffraction enhanced x-ray imaging", Phys. Med. Biol. 42, 1997, pp. 2015-2025.

Wilkins et a., "Phase-contrast imaging using polychromatic hard X-rays", Nature 384, 1996, pp. 335-338.

V. Lehmann, The Physics of Macropore Formation In low Doped n-Type Silicon, J. Electrochemical Soc. 140 (10), 1993, pp. 2836-2843.

Bergmann, Schäfer, "Lehrbuch der Experimentalphysik", vol. 1, Mechanik, Akustik, Wärme, De Gruyter, Berlin, 1970, pp. 542-554.

Shack et al., J. Opt. Soc. Am. 61, 1971, p. 656.

Platt et al., "History and Principles of Shack-Hartmann Wavefront Sensing", Journal of Refractive Surgery, vol. 17, 2001, pp. 573-577.

F. Roddier, "Variations on a Hartmann theme", Opt. Eng. 29, 1990, pp. 1239-1242.

Primot et al., "Deconvolution from wave-front sensing: a new technique for compensating turbulence-degraded images", J. Opt. Soc. Am. 7(9), 1990, pp. 1598-1608.

J. C. Wyant, "White Light Extended Source Shearing Interferometer", Appl. Opt. 13, 1974, pp. 200-202.

C. L. Kollopoulos, "Radial grating lateral shear heterodyne Interferometer", Appl. Opt. 19, 1980, pp. 1523-1528.

J. Primot, L. Songo, "Achromatic three-wave (or more) lateral shearing interferometer", J. Opt. Soc. Am. A. 12(12), 1995, pp. 2679-2685.

J. Primot, "Theoretical description of Shack-Hartmann wave-front sensor", Optics Communications, 222, 2003, pp. 81-92.

V. Ronchi, "Forty Years of History of Grating Interferometer", Appl. Opt., 3(4), 1964, pp. 437-451.

Schroer et al., "Hard x-ray nanoprobe based on refractive x-ray lenses", Appl. Phys. Lett. 87, 124103, 2005.

M. Bavdaz, N. Gurker, "Coded Imaging X-ray Microprobe", X-Ray Spectrometry, 22, 1993, pp. 65-70.

Momose et al. "Tomographic image reconstruction using X-ray phase information", SPIE, vol. 2708, pp. 674-684.

Barty et al., "Time-gated medical imaging with ultrafast laser plasma x-rays", SPIE, vol. 2523, pp. 286-298.

C. J. Kotre, I. P. Birch, "Phase contrast enhancement of x-ray mammography: a design study", Phys. Med. Biol., 44, 1999, pp. 2853-2866.

Arfelli et al, "Low-dose phase contrast x-ray medical imaging", Phys. Med. Biol. 43, 1998, pp. 2845-2852.

Herrlin et al., "Contrast-Enhanced Radiography by Differential Absorption Using a Laser-Produced X-Ray Source", Investigative Radiology 32, 1997, pp. 306-310.

Grätz et al., "Time-Gated Imaging in Radiology: Theoretical and Experimental Studies", IEEE J. of selected Topics in Quantum Electronics, 2(4), 1996, pp. 1041-1048.

Murnane et al., "Ultrafast X-ray Pulses from Laser-Produced Plasmas", Science, vol. 251, 1991, pp. 531-536.

Krol et al., "Laser-based microfocused x-ray source for mammography: Feasibiliy study", Med. Phys. 24(5), 1997, pp. 725-732.

Piestrup et al., "A design of mammography units using a quasiminichromatic x-ray source", Review of Scientific Instruments, 72(4), 2001, pp. 2159-2170.

C. G. Schroer, B. Lengler, "Focusing Hard X Rays to Nanometer Dimensions by Adiabatically Focusing Lenses", Phys. Rev. Lett. 94, 054802, 2005.

* cited by examiner

FOCUS/DETECTOR SYSTEM OF AN X-RAY APPARATUS FOR GENERATING PHASE CONTRAST RECORDINGS

PRIORITY STATEMENT

The present application hereby claims priority under 35 U.S.C. §119 on German patent applications number DE 10 2006 004 976.4 filed Feb. 1, 2006, and number DE 10 2006 015 358.8 filed Apr. 3, 2006, the entire contents of each of which is hereby incorporated herein by reference.

FIELD

Embodiments of the invention generally relate to a focus/detector system of an X-ray apparatus, such as one for generating projective and tomographic phase contrast recordings, including a beam source, a detector arrangement for detecting the X-radiation and a set of X-ray optical gratings, for example, for determining the phase shift when the X-radiation passes through a subject.

BACKGROUND

In computer tomography, tomographic recordings of a subject, in particular a patient, are generally made with the aid of absorption measurements of X-rays which pass through the subject, a radiation source generally being moved circularly or spirally around the subject and a detector on the opposite side from the radiation source, usually a multi-line detector with a multiplicity of detector elements, measuring the absorption of radiation when it passes through the subject. For tomographic image compilation, tomographic section images or volume data are reconstructed from the measured absorption data of all geometrical rays. Absorption differences in objects can be represented very well by these computer tomographic recordings, but regions with similar chemical composition, which naturally also have a similar absorptivity, can be represented only with insufficient detail.

It is furthermore known that the effect of the phase shift when a ray passes through a subject is substantially stronger than the absorption effect of the material through which the radiation has passed. Such phase shifts are measured in a known way by using two interferometric gratings.

With respect to these interferometric measurement methods, reference is made for example to "X-ray phase imaging with a grating interferometer, T. Weitkamp et al., $8^{th}$ Aug. 2005/Vol. 12, No. 16/OPTICS EXPRESS". In this method, coherent X-radiation passes through a subject, then is guided through a grating pair and the radiation intensity is measured immediately after the second grating. The first grating generates an interference pattern, which forms an image of a Moiré pattern with the aid of the second grating on the detector lying behind. If the second grating is displaced slightly, then this likewise causes a displacement of the Moiré pattern, i.e. a change of the local intensity in the detector lying behind, which can be determined relative to the displacement of the second grating. If the intensity changes are plotted for each detector element of this grating, i.e. for each ray, as a function of the displacement distance of the second grating, then the phase shift of the respective ray can be determined. A problem, making it unsuitable for carrying out computer tomography of sizeable objects, is that this method requires a very small radiation source since coherent radiation is needed for imaging the interference pattern.

The method presented in the document cited above requires either a radiation source with an extremely small focus, so that there is a sufficient degree of spatial coherence in the radiation used. When using such a small focus, however, then a sufficient dose power for examining a sizeable object is in turn not available. It is nevertheless also possible to use monochromatic coherent radiation, for example synchrotron radiation as the radiation source, but this makes the CT system very expensive to construct so that widespread application is not possible.

This problem can be circumvented by arranging a first absorption grating inside the focus/detector combination in the beam path, immediately after the focus. The alignment of the grating lines is in this case parallel to the grating lines of the interference grating which follows after the subject.

The slits of the first grating generate a field of individually coherent rays with a particular energy, which is sufficient for generating the interference pattern known per se with the aid of the phase grating arranged behind the object in the beam direction.

In this way, it is possible to use radiation sources which have extents that correspond to normal X-ray tubes in CT systems or transmitted-light X-ray systems so that, for example, even well-differentiated soft tissue tomographs can now be made in the field of general medical diagnosis.

When producing such an X-ray device for measuring the phase shift on large objects, for example a patient, it has been found that a fundamental problem consists in producing sufficiently large phase and analysis gratings so that the large detectors necessary for such examinations can thereby be covered. Another problem is that the requisite mechanism for displacing the analysis grating is difficult to handle, especially when used in a computer tomograph in which the detector rotates at a high speed, so that with excessively large X-ray optical gratings merely the instability of the grating itself can entail movements so large that they lead to strong errors in recording the phase shift.

SUMMARY

In at least one embodiment of the invention, a focus/detector system is provided for an X-ray apparatus for generating projective or tomographic phase contrast recordings, which provides the opportunity to make do with X-ray optical gratings of smaller size and at the same time places lesser demands on the mechanical stability of the gratings The inventors have discovered that the focus/detector system, in at least one embodiment, can be constructed modularly so that a single source grating is used for generating the quasi-coherent radiation in the beam path of the focus on the one hand, a modularly constructed set of phase/analysis gratings being used on the detector side, each individual grating having a size which is readily producible by normal wafer production. These will generally be wafer sizes of approximately 5×5 $cm^2$, or similarly designed wafers of the order of 15×2 $cm^2$. By using such compact gratings, it is possible to construct individual modules which consist of a focus-side phase grating, a subsequent analysis grating and a sub-detector, which is arranged directly behind the analysis grating that in turn consists of a multiplicity of individual detector elements.

Depending on the construction of the grating/detector modules, it is then possible to displace the analysis grating of this module individually in order to measure the phase shift of a ray passing through the subject. For a line of detector modules, it is nevertheless also possible to provide a common drive for the analysis gratings arranged there. It should however be pointed out that the drive is not a categorical requirement for a grating/detector module according to at least one embodiment of the invention, since, with detectors that spatially resolve sufficiently, it is not absolutely necessary to displace the analysis grating in order to measure the phase shift.

According to the basic concept of at least one embodiment of the invention, the Inventors provide a focus/detector system of an X-ray apparatus for generating projective or tomographic phase contrast recordings, comprising:

a beam source having a focus and a focus-side source grating, which is arranged in the beam path and generates a field of ray-wise coherent X-rays, and a detector arrangement having a multiplicity of detector modules arranged next to one another, which respectively comprise arranged successively in the beam direction:

at least one phase grating for generating a first interference pattern, an analysis grating for generating a further interference pattern, and detector elements arranged flat, the individual grating lines of all gratings being aligned mutually parallel.

As described above, such a construction of a focus/detector system allows the use of relatively small X-ray optical gratings, which are readily producible by conventional wafer production.

In principle, it is possible to configure the module variants differently; for example, the grating surfaces formed by the grating lines on the phase and analysis gratings of the modules may be aligned mutually parallel, or it is possible to respectively align the grating surfaces perpendicularly to a ray which extends from the focus to the detector module and intersects the grating surfaces.

The variant mentioned first thus leads to a common grating surface both for the phase grating and for the subsequent analysis grating, and optionally for the detector array following on from this. Such an embodiment may be advantageous particularly when using a C-arc system or when used in X-ray systems for compiling projective recordings. A problem here may be that not all modules of a sizeable detector system can be designed identically. Thus, although it is possible to use identical grating systems, it is nevertheless necessary to "package" the individual gratings in differently configured housings.

The other variant mentioned second offers the opportunity that, for example in a CT detector, the individual grating planes can be arranged tangentially to a sphere or cylinder surface around the focus. For example, the arrangement may be such that the ray which respectively intersects the grating surfaces perpendicularly is the central ray which intersects the grating surfaces at their respective midpoint.

According to another variant of the arrangement, the grating/detector modules may be arranged so that the midpoints of all phase grating surfaces have the same distance from the focus. Thus, the grating/detector modules are thus arranged spherically around the focus over a particular segment. An arrangement in which the midpoints of all phase grating surfaces and/or the midpoints of all analysis grating surfaces and/or the midpoints of all detector surfaces of the individual modules have the same distance from the focus may be advantageous here. In this variant, it is respectively assumed that the grating surfaces are formed to be flat per se. It is nevertheless also possible for the phase grating surfaces and/or the analysis grating surfaces and/or the detector surfaces of the individual grating/detector modules to be designed according to a spherical surface segment with the focus as the midpoint.

According to another variant of the focus/detector system according to at least one embodiment of the invention, at least one device may be provided for relative displacement of at least one analysis grating with respect to the phase gratings perpendicularly to the beam direction and perpendicularly to the longitudinal direction of the grating lines, which acts on at least two analysis gratings of at least two grating/detector modules. Thus, in the focus/detector system, there is a drive device or adjustment device which drives at least two analysis gratings of different detector modules. Such an embodiment may for example be used when a plurality of analysis gratings are arranged on the same radius or on the same plane, so that the displacement of one analysis grating takes place simultaneously with the offset of the other analysis grating arranged on this plane or sphere.

According to another variant, a separate drive device may be provided per grating/detector module for the analysis grating, so that this drive device only moves this analysis grating. In respect of the drive device, besides electric motor drive devices it is also possible for example to use a piezo element, which on the one hand allows very exact displacement travels and on the other hand is not very susceptible to the high centrifugal forces which act in a CT detector.

Considering the arrangement of the individual grating/detector modules in the focus/detector system, these may for example be arranged in a checkerboard fashion. This will be a preferred variant for focus/detector systems which are used for a C-arc system or for use in X-ray systems to generate projective recordings.

An arrangement in which the individual grating/detector modules form a single line, as seen in projection from the focus, is particularly preferred for CT systems having detectors which are installed in a gantry. Such detector modules then do not have a square or approximately square design, rather they are aligned in the z direction of the CT system so that the detector, which is designed as a multiline detector owing to the detector elements arranged next to one another in multiple lines, nevertheless comprises only a single line of detector modules. It should however be pointed out that other construction options also lie within the scope of the invention.

According to at least one embodiment of the invention, the grating/detector modules should be designed and arranged so that each grating/detector module and its grating arrangement—particularly in conjunction with the source grating on the side of the focus—satisfies the following geometrical conditions:

$$p_0 = p_2 \times \frac{l}{d},$$

$$p_1 = 2 \times \frac{p_0 \times p_2}{p_0 + p_2}$$

$$d = \frac{l \times d^=}{l - d^=} \text{ with } d^= = \frac{1}{2} \times \left(\frac{p_1^2}{4\lambda}\right),$$

$$h_1 = \frac{\lambda}{2(n-1)}.$$

Here:
$p_0$ = grating period of the source grating $G_0$,
$p_1$ = grating period of the phase grating $G_1$,
$p_2$ = grating period of the analysis grating $G_2$,
$d$ = distance from the phase grating $G_1$ to the analysis grating $G_2$ in fan beam geometry,
$d^=$ = distance from the phase grating $G_1$ to the analysis grating $G_2$ with parallel geometry, l=distance from the source grating $G_0$ to the phase grating $G_1$,
λ=selected wavelength of the radiation,
$h_1$ =bar height of the phase grating $G_1$ in the beam direction,
n=refractive index of the grating material of the phase grating.

According to the basic concept of at least one embodiment of the invention, the Inventors propose that the focus/detector system as described above be used, for example, in an X-ray system for generating projective phase contrast recordings with at least one focus/detector system.

The focus/detector systems may furthermore be utilized in C-arc systems which are used to generate projective and tomographic phase contrast recordings.

Furthermore, and particularly preferably, the Inventors propose that the described focus/detector systems be used in X-ray CT systems for generating tomographic phase contrast recordings, in which case these X-ray CT systems may have at least one focus/detector system of the type described above, or even a plurality of focus/detector systems which are respectively arranged on a rotatable gantry. If a plurality of focus/detector systems are used, then these may be arranged both angularly offset and offset in the direction of the system axis of the CT system. Combinations of this also lie within the scope of the invention.

The scope of the invention also encompasses, in at least one embodiment, a method for generating tomographic recordings of a subject, preferably a patient, wherein at least the following method steps are carried out:

the subject is scanned circularly or spirally with at least one modularly constructed focus/detector system of the type described above, the phase shift of the rays when passing through the subject being determined by at least three intensity measurements with analysis gratings respectively arranged offset, for rays which cannot be measured or cannot be measured accurately owing to the modular construction of the detector, the phase shift is interpolated by neighboring values, tomographic phase contrast recordings are reconstructed by the rays' phase shifts measured and determined by interpolation.

This compensates for the problem of the modular construction of such focus/detector systems, according to which somewhat nonuniform scanning takes place because of the non-arbitrary packing density in the region of the impact surfaces of the detector modules. Corresponding equalization can be obtained by appropriate interpolation of these non-measured values.

BRIEF DESCRIPTION OF THE DRAWINGS

The invention will be explained in more detail below with reference to example embodiments with the aid of the figures, only the features necessary for understanding the invention being represented. Here, the following references are used: 1: CT system; 2: first X-ray tube; 3: first detector; 4: second X-ray tube; 5: second detector; 6: gantry housing; 7: patient; 8: patient support; 9: system axis; 10: control and computation unit; 11: memory; 12: piezo element; 13: spring element; 14: wall of the grating/detector module; D: entire detector; $D_i$: detector of a grating/detector module; $D_x$: detector module; d: distance from the phase grating $G_1$ to the analysis grating $G_2$ in fan beam geometry; $d^=$: distance from the phase grating $G_1$ to the analysis grating $G_2$ with parallel geometry; $F_1$: focus; $G_0$: source grating; $G_1$, $G_{1i}$: phase grating; $G_2$, $G_{2i}$: analysis grating; $G_{Dx}$: grating/detector module; $h_0$: bar height of the source grating; $h_1$: bar height of the phase grating; $h_2$: bar height of the analysis grating; l: distance from the source grating $G_0$ to the phase grating $G_1$; n: refractive index of the grating material of the phase grating; P: patient; $p_0$: grating period of the source grating; $P_1$: grating period of the phase grating; $p_2$: grating period of the analysis grating; $Prg_x$: program; S: system axis; $X_G$: offset of the analysis grating; λ: wavelength of the X-rays.

The figures show the following in detail.

DETAILED DESCRIPTION OF THE EXAMPLE EMBODIMENTS

It will be understood that if an element or layer is referred to as being "on", "against", "connected to", or "coupled to" another element or layer, then it can be directly on, against, connected or coupled to the other element or layer, or intervening elements or layers may be present. In contrast, if an element is referred to as being "directly on", "directly connected to", or "directly coupled to" another element or layer, then there are no intervening elements or layers present. Like numbers refer to like elements throughout. As used herein, the term "and/or" includes any and all combinations of one or more of the associated listed items.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

Figure 1:
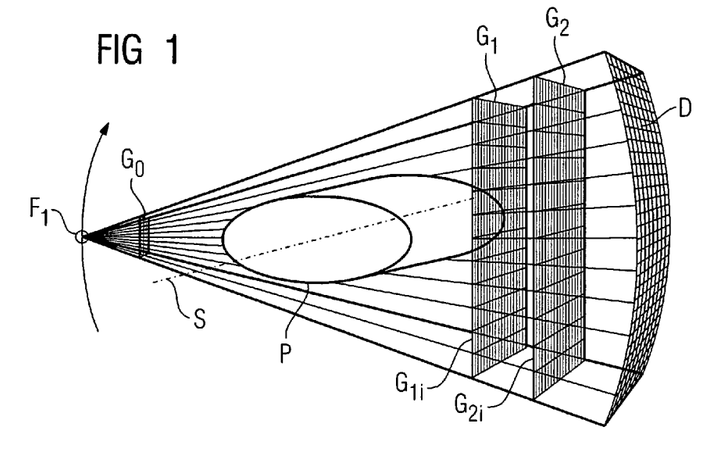
FIG. 1: schematic 3D representation of a focus/detector system with a grating set for determining phase shifts.

FIG. 1 shows a schematic 3D representation of a focus/detector system of an X-ray CT with a patient P lying in the beam direction as the subject. The focus $F_1$ and the detector D are arranged on a gantry (not shown here) and move circularly about the system axis S. If a linear movement of the patient P in the system axis direction is additionally carried out during the rotation of the focus/detector system, then this leads to spirally shaped scanning of the patient P which is known per se. Three X-ray optical gratings $G_0$, $G_1$ and $G_2$ are arranged in the beam path of the focus/detector system, the first grating $G_0$—which is also referred to as a source grating—being applied in the immediate vicinity of the focus $F_1$ and having the X-radiation pass through it. In the propagation direction of the X-radiation, this is followed by the actual subject or patient P.

Before the detector D lying on the other side of the system axis S, there first follows the second grating $G_1$ referred to as a phase grating. This is followed in the radiation direction by the third grating $G_2$, referred to as an analysis grating, which is advantageously arranged immediately in front of the detector D. The detector D comprises at least one line of a multiplicity of detector elements, and the detector D is preferably constructed as a multiline detector which is equipped with a multiplicity of detector lines arranged parallel, each with a multiplicity of detector elements. During the scan, connecting lines between the focus $F_1$ and the individual detector elements respectively represent an X-ray arranged in space, the intensity variation of which is measured by the respective detector element.

It should be pointed out that in the case of so-called C-arc equipment which also falls within the class of CT systems mentioned here, the detector D is not designed as a cylinder segment around the focus $F_1$ as shown, but has a flat shape. In projective X-ray systems which do not carry out any movement about the subject during the scans, the detector D is likewise generally designed to be flat.

The line orientation of the gratings $G_0$ to $G_2$ is designed so that the grating lines of all three gratings extend mutually parallel. It is advantageous, but not necessary, for these grating lines to be furthermore oriented parallel or perpendicular to the system axis S. In the variants shown, the gratings $G_0$ to $G_2$ are designed to be flat and aligned perpendicularly to the midline between the focus and detector midpoints.

The first grating $G_0$ has a grating line period $p_0$ and a grating bar height $h_0$. The gratings $G_1$ and $G_2$ are correspondingly provided with a height $h_1$ and $h_2$, respectively, and a period $p_1$ and $p_2$, respectively. For the function of the method according to the invention, it is necessary for the distance l between the gratings $G_0$ and $G_1$ and the distance d between the gratings $G_1$ and $G_2$ to be in a particular mutual ratio. Here, $$p_0 = p_2 \times \frac{l}{d}$$

The distance of the detector $D_1$ with its detector elements from the last grating $G_2$ is not essential. The height $h_1$ of the bars of the phase grating should be selected so that the following formula is satisfied according to the wavelengths in question, i.e. the relevant energy of the X-radiation, and in relation to the respective grating material:

$$h_1 = \frac{\lambda}{2(n-1)}$$

Here, n denotes the refractive index of the grating material and $\lambda$ denotes the wavelengths of the X-radiation, at which the phase shift is intended to be measured. This grating is advantageously adjusted to an energy which corresponds to a characteristic line in the X-ray spectrum of the anode being used.

The height $h_2$ of the analysis grating must be sufficient in order to generate effective absorption differences between the bars through which the X-radiation passes and the substantially free positions of the grating, in order to obtain a corresponding Moiré pattern on the rear side.

Furthermore, the following geometrical relationships also apply in the grating set:

$$p_1 = 2 \times \frac{p_0 \times p_2}{p_0 + p_2}$$

and $$d = \frac{l \times d^=}{l - d^=} \text{ with } d^= = \frac{1}{2} \times \left(\frac{p_1^2}{4\lambda}\right),$$

where $d=$ is the distance from the phase grating $G_1$ to the analysis grating $G_2$ with the assumption of a parallel geometry, and d is the distance from the phase grating $G_1$ to the analysis grating $G_2$ in a fan beam geometry.

As can be seen from this presentation, the dimensions of the phase grating $G_1$ and of the analysis grating $G_2$ assume sizes which can scarcely be represented via the normal production of wafers, or at least are no longer cost-effectively feasible. In the context of an embodiment of the invention, it is therefore proposed that the gratings $G_1$ and $G_2$ should be divided up modularly. This may for example be done as indicated in FIG. 1, i.e. the gratings $G_1$ and $G_2$ may be subdivided in the direction of the system axis so as to produce elongate grating elements, although these now have to be fastened modularly in the focus/detector element. In the schematic representation of FIG. 1, the individual phase and analysis gratings are arranged so that the totality of all phase gratings lie together on a common plane, while the analysis gratings of the modules likewise form a common grating plane.

Figure 2:
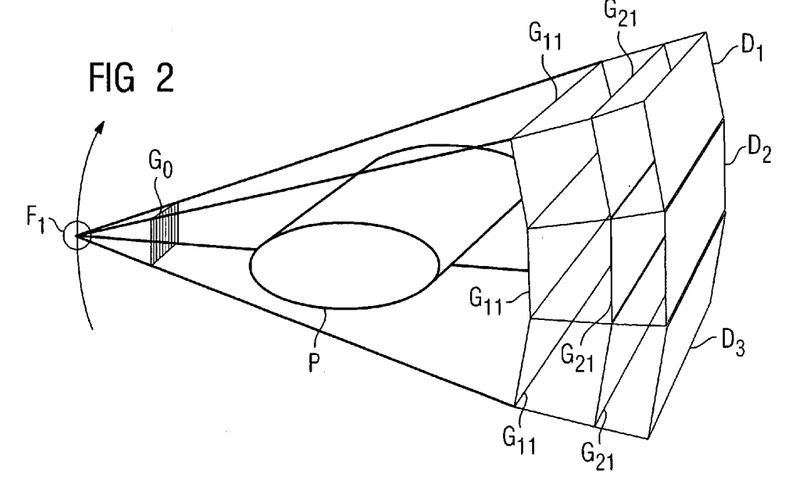
FIG. 2: schematic 3D representation of a focus/detector system with three detector/grating modules.

FIG. 2 represents another variant. A single source grating $G_0$ is likewise presented in the focus/detector system shown here—similarly as in FIG. 1, but the focus/detector system on the detector side includes three grating/detector modules, the phase and analysis gratings and the surfaces of the detector elements of each module being aligned mutually parallel and all three grating/detector modules being arranged in a fan shape with respect to the focus $F_1$. Each individual module includes the phase grating $G_{1x}$ an analysis grating $G_{2x}$, which follows in the beam direction, with the detector module $D_x$ following immediately after it, each individual detector module consisting of a multiplicity of detector elements arranged in a checkerboard fashion, although these are not shown here.

Figure 3:
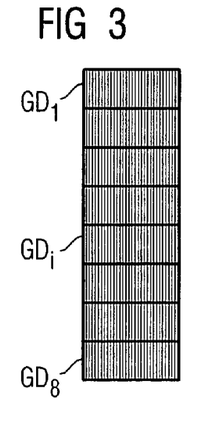
FIG. 3: plan view of a CT detector including eight grating/detector modules.

If such a construction of the focus/detector is refined so that a plurality of detector modules are used, then, as seen in projection from the focus, this gives an arrangement of that grating/detector modules as represented in FIG. 3. Eight grating/detector modules arranged in a fan shape are shown here, the alignment of the grating lines in these grating/detector modules being perpendicular to the system axis.

Figure 4:
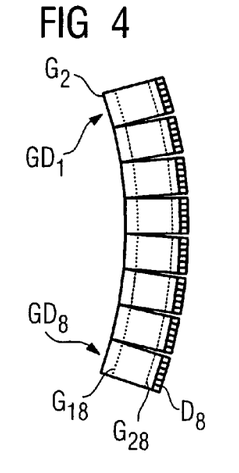
FIG. 4: cross section perpendicular to the system axis of the grating/detector modules of the CT detector in FIG. 3.

If this arrangement is cut perpendicularly to the system axis, then a representation as in FIG. 4 is obtained. This FIG. 4 shows the fan-like arrangement of eight grating/detector modules $G_{D1}$ to $G_{D8}$, which are designed rectangularly in this section and respectively comprise a phase grating $G_{1x}$ with a subsequent analysis grating $G_{2x}$, and a detector module $D_x$. As can be seen from this figure, with this design a gap is respectively formed on the other side from the focus in the region of the detector modules $D_x$. Similar gaps may for example result merely from a finite thickness of module housings. Such gaps also lead to gaps in the scan, or at least to scanning errors and artifacts. For this purpose, it is advantageous for such regions to be bridged by interpolations or matched to one another so that artifacts are avoided in the imaging. This may advantageously be done directly when compiling full projection data sets, or the completed volume data sets may be processed accordingly.

Figure 5:
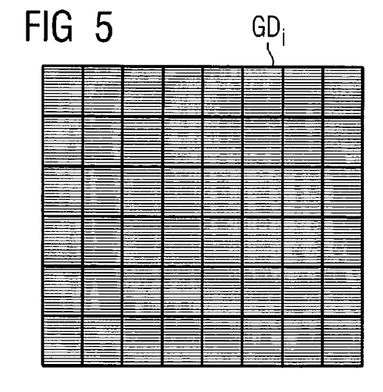
FIG. 5: plan view of a detector for taking projective phase contrast recordings, including an 8×6 grating/detector module assembled in checkerboard fashion.

While the image of a detector for a CT system with a revolving gantry is shown in FIGS. 3 and 4, FIG. 5 shows the construction of a focus/detector system for a C-arc system or a simple projective X-ray system. The individual grating/detector modules are arranged in a checkerboard fashion here, the alignment of the grating lines of all gratings used being the same and corresponding to the alignment of the source grating.

Figure 6:
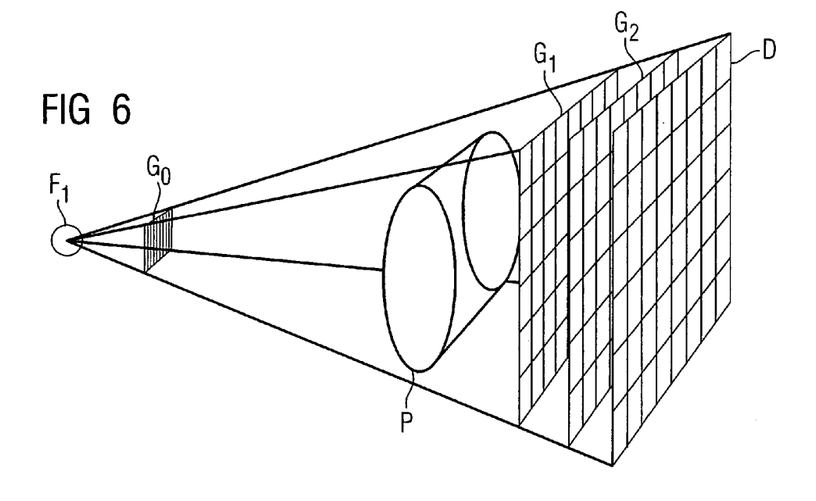
FIG. 6: 3D representation of a focus/detector system of a C-arc system with flat gratings and a flat detector.

The arrangement of such grating/detector modules in the overall focus/detector system is represented in FIG. 6. This shows the focus/detector module according to the invention with a detector D aligned so that it is flat and approximately square, which includes a multiplicity of grating/detector modules that in total form the surface of the phase grating $G_1$ and the subsequent analysis grating $G_2$.

Figure 7:
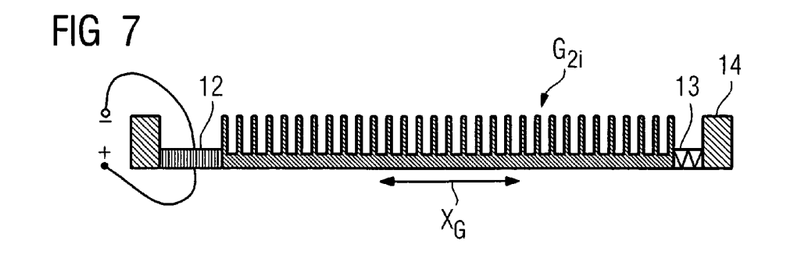
FIG. 7: section through an analysis grating with a displacement device.

FIG. 7 shows a detailed view of a grating/detector module in the region of the analysis grating in a section perpendicular to the grating lines. The analysis grating $G_2$ is clamped on both sides in the walls 14 of the grating/detector module, a piezo element 12 being arranged on one side between the analysis grating $G_{2i}$ and the wall 14 and a spring element 13 being provided on the opposite side. When a corresponding voltage is applied to the piezo element 12, then this leads to a longitudinal displacement $X_G$ of the analysis grating $G_{2i}$, which is necessary in order to determine the phase shift of the ray at this position with the aid of at least three measurements with the analysis grating deflected differently.

Figure 8:
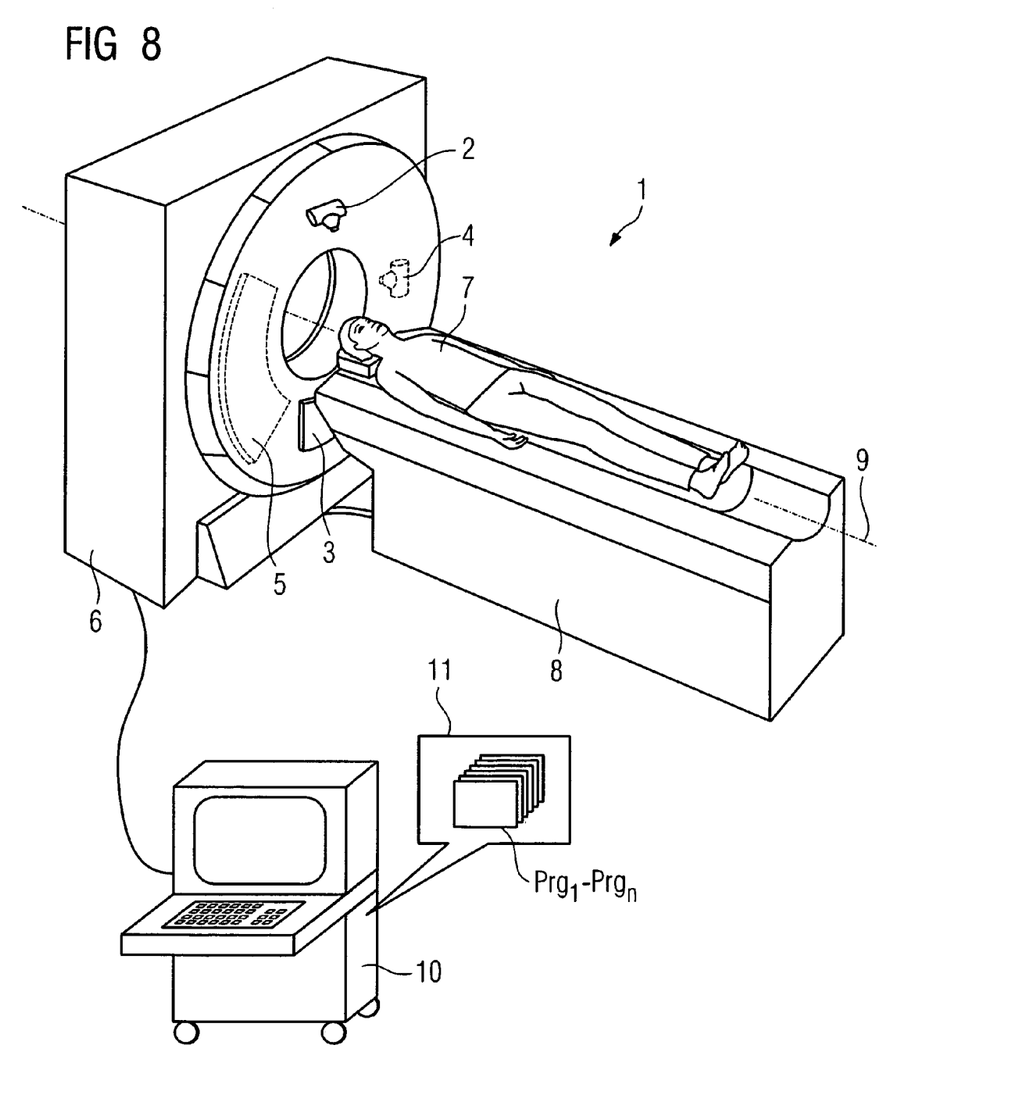
FIG. 8: X-ray CT system with focus/detector systems according to an embodiment of the invention in 3D view.

A complete computer CT system for carrying out the method according to the invention is represented in FIG. 8. This shows the CT system 1 which includes a first focus/detector system with an X-ray tube 2 and a detector 3 lying opposite, which are arranged in a gantry (not shown) in a gantry housing 6. A grating system according to FIGS. 1 to 3 is arranged in the beam path of the first focus/detector system 2, 3 so that the patient 7, who lies on a patient support 8 displaceable along the system axis 9, can be displaced into the beam path of the first focus/detector system and scanned there. The CT system is controlled by a computation and control unit 10 in which programs $Prg_1$ to $Prg_n$ are stored in a memory 11, which carry out the method according to an embodiment of the invention as described above and reconstruct corresponding tomographic images from the measured ray-dependent phase shifts and absorptions.

Instead of the single focus/detector system, a second focus/detector system may optionally be arranged in the gantry housing. This is indicated in FIG. 8 by the X-ray tube 4 shown in dashes and the detector 5 represented in dashes.

It is to be understood that the features of the invention as mentioned above may be used not only in the combination respectively indicated, but also in other combinations or in isolation, without departing from the scope of the present invention.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A focus/detector system of an X-ray apparatus for generating at least one of projective and tomographic phase contrast recordings, the system comprising:
    a beam source, including a focus and a focus-side source grating, arranged in the beam path to generate a field of ray-wise coherent X-rays; and
    a detector arrangement including a multiplicity of grating/detector modules arranged next to one another, which respectively comprise arranged successively in the beam direction:
        at least one phase grating to generate a first interference pattern,
        an analysis grating to generate a further interference pattern, and
        detector elements arranged flat, the individual grating lines of all gratings being aligned mutually parallel.

2. The focus/detector system as claimed in claim 1, wherein the grating surfaces formed by the grating lines on the phase and analysis gratings of the module are aligned mutually parallel.

3. The focus/detector system as claimed in claim 1, wherein the grating surfaces are respectively aligned perpendicularly to a ray which extends from the focus to the grating/detector module and intersects the grating surfaces.

4. The focus/detector system as claimed in claim 3, wherein the ray which respectively intersects the grating surfaces perpendicularly is the central ray which intersects the grating surfaces at their respective midpoint.

5. The focus/detector system as claimed in claim 4, wherein the grating/detector modules are arranged so that the midpoints of all phase grating surfaces have the same distance from the focus.

6. The focus/detector system as claimed in claim 4, wherein the grating/detector modules are arranged so that the midpoints of all analysis grating surfaces have the same distance from the focus.

7. The focus/detector system as claimed in claim 4, wherein the grating/detector modules are arranged so that the midpoints of all analysis grating surfaces have the same distance from the focus.

8. The focus/detector system as claimed in claim 4, wherein the grating/detector modules are arranged so that the midpoints of all detector surfaces, consisting of the sum of detector elements arranged flat, have the same distance from the focus.

9. The focus/detector system as claimed in claim 4, wherein the phase grating surfaces are respectively formed on a spherical surface segment with the focus as the midpoint.

10. The focus/detector system as claimed in claim 9, wherein the analysis grating surfaces are respectively formed on a spherical surface segment with the focus as the midpoint.

11. The focus/detector system as claimed in claim 4, wherein the analysis grating surfaces are respectively formed on a spherical surface segment with the focus as the midpoint.

12. The focus/detector system as claimed in claim 4, wherein the detector surfaces of a grating/detector module, consisting of the sum of detector elements arranged flat, respectively extend over a spherical surface segment with the focus as the midpoint.

13. The focus/detector system as claimed in claim 1, wherein at least one device is provided for relative displacement of at least one analysis grating with respect to the phase gratings perpendicularly to the beam direction and perpendicularly to the longitudinal direction of the grating lines, which acts on at least two analysis gratings of at least two grating/detector modules.

14. The focus/detector system as claimed in claim 1, wherein one device per grating/detector module is provided for relative displacement of the analysis grating of this grating/detector module with respect to the phase grating of this grating/detector module perpendicularly to the beam direction and perpendicularly to the longitudinal direction of the grating lines.

15. The focus/detector system as claimed in claim 1, wherein the grating/detector modules are arranged in a checkerboard fashion as seen in projection from the focus.

16. The focus/detector system as claimed in claim 1, wherein the grating/detector modules form a single line as seen in projection from the focus.

17. The focus/detector system as claimed in claim 1, wherein the grating/detector modules are designed and arranged so that each grating/detector module and its grating arrangement satisfies the following geometrical conditions:

$$p_0 = p_2 \times \frac{l}{d},$$

$$p_1 = 2 \times \frac{p_0 \times p_2}{p_0 + p_2},$$

$$d = \frac{l \times d^=}{l - d^=} \text{ with } d^= = \frac{1}{2} \times \left(\frac{p_1^2}{4\lambda}\right),$$

$$h_1 = \frac{\lambda}{2(n-1)}.$$

where:
$p_0$=grating period of the source grating $G_0$,
$p_1$=grating period of the phase grating $G_1$,
$p_2$=grating period of the analysis grating $G_2$,
d=distance from the phase grating $G_1$ to the analysis grating $G_2$ in fan beam geometry,
$d^=$=distance from the phase grating $G_1$ to the analysis grating $G_2$ with parallel geometry,
l=distance from the source grating $G_0$ to the phase grating $G_1$,
$\lambda$=selected wavelength of the radiation,
$h_1$ =bar height of the phase grating $G_1$ in the beam direction,
n=refractive index of the grating material of the phase grating.

18. An X-ray system for generating projective phase contrast recordings including at least one focus/detector system as claimed in claim 1.

19. The X-ray system as claimed in claim 18, wherein a computation unit is provided for controlling the analysis grating and calculating the phase shift from a plurality of intensity measurements of the same beam with differently offset analysis gratings.

20. An X-ray C-arc system for generating projective and tomographic phase contrast recordings including at least one focus/detector system as claimed in claim 1, arranged on a C-arc rotatable about a subject.

21. An X-ray CT system for generating tomographic phase contrast recordings including at least one focus/detector system as claimed in claim 1, arranged on a gantry rotatable about a subject.

22. A method for generating tomographic recordings of a subject, the method comprising:
   scanning the subject at least one of circularly and spirally with at least one modularly constructed focus/detector system a phase shift of rays passing through the subject being determined by at least three intensity measurements with analysis gratings respectively arranged offset;
   interpolating the phase shift using neighboring values for rays which cannot be measured or cannot be measured accurately due to the modular construction of the detector; and
   reconstructing tomographic phase contrast recordings using the rays' phase shifts measured and determined by interpolation; wherein the focus/detector system includes,
      a beam source, including a focus and a focus-side source grating, arranged in the beam path to generate a field of ray-wise coherent X-rays; and
      a detector arrangement including a multiplicity of grating/detector modules arranged next to one another, which respectively comprise arranged successively in the beam direction:
         at least one phase grating to generate a first interference pattern,
         an analysis grating to generate a further interference pattern, and
         detector elements arranged flat, the individual grating lines of all gratings being aligned mutually parallel.

23. A storage medium of an X-ray system, the storage medium containing program code that, when executed, carries out the method as claimed in claim 22 during operation of the X-ray system.

24. An X-ray system for generating projective phase contrast recordings, comprising:
   at least one focus/detector system for generating at least one of projective and tomographic phase contrast recordings, the system including,
      a beam source including a focus and a focus-side source grating, arranged in the beam path to generate a field of ray-wise coherent X-rays, and
      a detector arrangement including a multiplicity of grating/detector modules arranged next to one another, which respectively comprise arranged successively in the beam direction:
         at least one phase grating to generate a first interference pattern,
         an analysis grating to generate a further interference pattern, and detector elements arranged flat, the individual grating lines of all gratings being aligned mutually parallel; and a computation and control unit, containing program code that, when executed on the computation and control unit, the computation and control unit is configured to, scan the subject at least one of circularly and spirally with the at least one modularly constructed focus/detector system, the phase shift of the rays when passing through the subject being determined by at least three intensity measurements with analysis gratings respectively arranged offset, interpolate, the phase shift using neighboring values for rays which cannot be measured or cannot be measured accurately owing to the modular construction of the detector, and reconstruct tomographic phase contrast recordings using the rays' phase shifts measured and determined by interpolation.

* * * * *